United States Patent
Duxbury et al.

(10) Patent No.: US 9,931,864 B2
(45) Date of Patent: Apr. 3, 2018

(54) METHOD AND APPARATUS FOR FORMING AN IMAGE

(71) Applicants: Debrah Gail Duxbury, West Kelowna (CA); Nigel Duxbury, West Kelowna (CA)

(72) Inventors: Debrah Gail Duxbury, West Kelowna (CA); Nigel Duxbury, West Kelowna (CA)

( * ) Notice: Subject to any disclaimer, the term of this patent is extended or adjusted under 35 U.S.C. 154(b) by 0 days.

(21) Appl. No.: 15/220,291

(22) Filed: Jul. 26, 2016

(65) Prior Publication Data

US 2017/0136781 A1  May 18, 2017

Related U.S. Application Data

(60) Provisional application No. 62/255,304, filed on Nov. 13, 2015.

(51) Int. Cl.
| | |
|---|---|
| *B41J 3/407* | (2006.01) |
| *A61M 35/00* | (2006.01) |
| *B41K 1/00* | (2006.01) |
| *B41K 1/28* | (2006.01) |
| *B44D 2/00* | (2006.01) |
| *A45D 29/00* | (2006.01) |

(52) U.S. Cl.
CPC ............ *B41J 3/4073* (2013.01); *A61M 35/00* (2013.01); *A61M 35/003* (2013.01); *B41K 1/00* (2013.01); *B41K 1/28* (2013.01); *B44D 2/002* (2013.01); *A45D 2029/005* (2013.01)

(58) Field of Classification Search
CPC ..... B41J 3/4073; B41F 17/001; A61M 35/003
See application file for complete search history.

(56) References Cited

U.S. PATENT DOCUMENTS

| | | | |
|---|---|---|---|
| 1,722,407 A | | 7/1929 | Bogaskie |
| 4,019,436 A | * | 4/1977 | Handweiler .......... B41F 17/001 |
| | | | 101/163 |

(Continued)

FOREIGN PATENT DOCUMENTS

| | | | | |
|---|---|---|---|---|
| CN | 2547513 | | 4/2003 | |
| FR | 2972138 A3 | * | 9/2012 | ............ A45D 29/00 |
| GB | 2427135 | | 11/2008 | |

OTHER PUBLICATIONS

Choi Dae Tong, MachineTranslationofFR 2972138 A3, 2011.*
Choi, MachineTranslationofFR 2972138 A3, 2012.*

*Primary Examiner* — Geoffrey Mruk
*Assistant Examiner* — Scott A Richmond
(74) *Attorney, Agent, or Firm* — Richard D. Okimaw (57) ABSTRACT

An apparatus for forming an image on the nail of a user comprises a handle body having an outer gripping surface and an inner surface defining a clear bore extending completely therethrough and an image transfer body formed of a transparent pliable material having an outer surface corresponding to the clear bore of the handle body and an image transfer surface extending from the handle body. A kit may include the apparatus and a plate containing at least one image location having a depression adapted to contain a portion of paint to be transferred to a user's nail. A user locates a portion of paint in depression of the plate, presses an image transfer surface on the image transfer body on the portion of paint to transfer the portion of paint to the image transfer surface and applies the image transfer surface to a nail of the user.

18 Claims, 6 Drawing Sheets

(56) References Cited

U.S. PATENT DOCUMENTS

| | | | | |
|---|---|---|---|---|
| 4,996,921 A * | 3/1991 | Hong | ........................ | B41K 1/52 |
| | | | | 101/327 |
| 5,227,205 A | 7/1993 | Dubrow et al. | | |
| 5,313,885 A | 5/1994 | Winston | | |
| 6,012,461 A | 1/2000 | McKew | | |
| 6,286,517 B1 | 9/2001 | Weber | | |
| 6,347,635 B1 * | 2/2002 | Jenkins | .................. | A45D 29/00 |
| | | | | 132/73 |
| 6,422,140 B1 | 7/2002 | Lookholder | | |
| 6,584,986 B2 | 7/2003 | Gindi | | |
| 6,708,614 B2 | 3/2004 | Lookholder | | |
| 2004/0200496 A1 * | 10/2004 | Choi | ....................... | A45D 29/00 |
| | | | | 132/200 |
| 2007/0144366 A1 * | 6/2007 | Ogino | ...................... | B41K 1/02 |
| | | | | 101/109 |
| 2008/0245314 A1 * | 10/2008 | Brodowski | ............. | A01N 25/34 |
| | | | | 119/651 |
| 2009/0211476 A1 * | 8/2009 | Inoue | ..................... | A63B 45/02 |
| | | | | 101/401 |
| 2011/0265809 A1 | 11/2011 | Jeon | | |
| 2013/0000665 A1 | 1/2013 | Choi | | |
| 2013/0139840 A1 | 6/2013 | Chang | | |
| 2013/0319444 A1 | 12/2013 | Pak | | |
| 2015/0158288 A1 * | 6/2015 | Gemelli | ................ | B41F 17/001 |
| | | | | 101/333 |
| 2017/0049216 A1 * | 2/2017 | Rhoades | ................ | A45D 40/30 |

* cited by examiner

METHOD AND APPARATUS FOR FORMING AN IMAGE

BACKGROUND OF THE INVENTION

1. Field of Invention

The present invention relates generally to personal decorating and in particular relates to a method and apparatus for forming an image on the nail of a user.

2. Description of Related Art

In personal fashion, many users enjoy applying colors and images to their nails for decorative effect. In particular, the application of images to the nails of a user provides a pleasing visual appearance. Conventionally, such images may be applied to the user's nail through painting freehand however it will be appreciated that such images require great skill to apply and have limited detail and consistency which may be applied. Additionally, images may be formed on the nail by applying a sticker or the like having the desired image. Disadvantageously, such stickers will form a raised image on the nail resulting in a uneven finish and are also limited to the images and colors published and available for purchase.

To address these deficiencies, the use of image stampers has been adopted whereby an image is formed on a plate using paint of a desired color. Thereafter a rubber stamp is utilized to pick up and transfer the image from the plate to the nail. A disadvantage of conventional stampers is that they block the image which the user is attempting to pick up thereby making precise placement of the image difficult. This is especially difficult in circumstances where a user wishes to form an image of multiple colors. In these circumstances, a user would commonly form each part of the image which is to be formed from a particular color as a separate image part. The stamper would then be used to transfer each image part to a common composite image on a transfer plate or the like. This allows the user to verify alignment of the image parts before transfer to the user's nail or start over if the image parts do not sufficiently align. It will be appreciated that such process may be time consuming and difficult to complete for detailed images having many colors.

SUMMARY OF THE INVENTION

According to a first embodiment of the present invention there is disclosed an apparatus for forming an image on the nail of a user comprising a handle body having an outer gripping surface and an inner surface defining a clear bore extending completely therethrough and an image transfer body formed of a transparent pliable material having an outer surface corresponding to the clear bore of the handle body and an image transfer surface extending from the handle body.

The image transfer surface may be convex. The image transfer surface may have a constant radius. The outer surface of the image transfer body may be tapered away from the image transfer surface. The outer surface of the image transfer body may be frustoconical. The outer surface of the image transfer body may have a constant cross section therealong. The image transfer body may be formed of a material selected from the group consisting of clear silicon and rubber.

The handle body may be substantially cylindrical. The handle body may be formed of a tubular wall having a consistent cross section therealong. The handle body may include an annular ledge extending substantially into the clear bore for supporting the image transfer body thereon. The annular ledge may be segmented around the clear bore.

According to a further embodiment of the present invention there is disclosed a method of forming an image on a nail of a user comprising locating a transparent pliable material within a clear bore extending completely through a handle, locating a portion of paint in a depression of a plate, pressing an image transfer surface on the image transfer body on the portion of paint to transfer the portion of paint to the image transfer surface and applying the image transfer surface to a nail of the user to transfer the paint to the nail.

The method may comprise repeating the steps of locating a portion of paint in a depression of a plate, pressing an image transfer surface on the image transfer body on the portion of paint to transfer the portion of paint to the image transfer surface a plurality of times.

According to a further embodiment of the present invention there is disclosed a kit for forming an image on the nail of a user comprising a plate containing at least one image location having a depression adapted to contain a portion of paint to be transferred to a user's nail and an apparatus for transferring said image. The apparatus comprises a handle body having an outer gripping surface and an inner surface defining a clear bore extending completely therethrough and an image transfer body formed of a transparent pliable material having an outer surface corresponding to the clear bore of the handle body and an image transfer surface extending from the handle body.

The plate includes a plurality of image locations each may have a depression adapted to contain a portion of paint. The plurality of image locations may be divided into a plurality of image groups. The plurality of image locations of each of the image groups may form a completed image when paint from each image location is overlaid on each other. The image groups may be aligned along a path across the plate.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
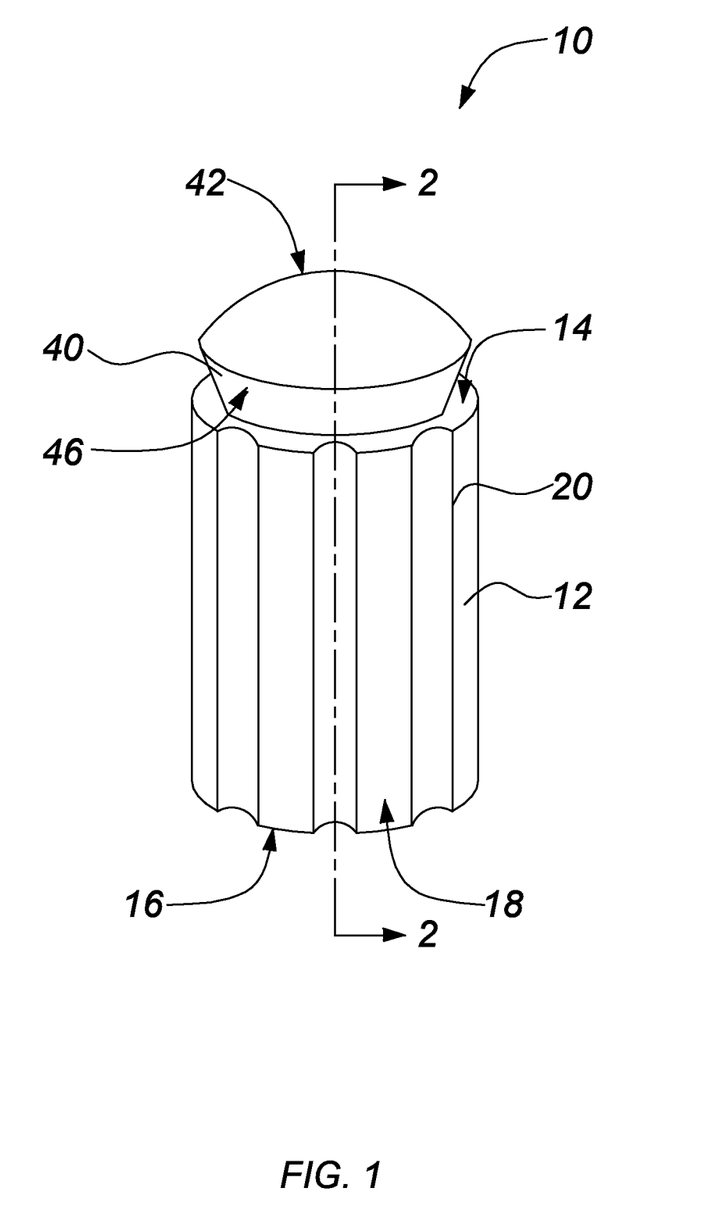
FIG. 1 is a perspective view of an apparatus for transferring images to the nail of a user according to a first embodiment of the present invention.

Referring to FIG. 1, an apparatus for forming an image on a nail according to a first embodiment of the invention is shown generally at 10. The apparatus comprises a handle body 12 and an image transfer body 40 located within one end thereof. As will be more fully described below, the image transfer body 40 is utilized to lift a portion of paint contained on an originating surface for transfer to the nail of the user.

Figure 2:
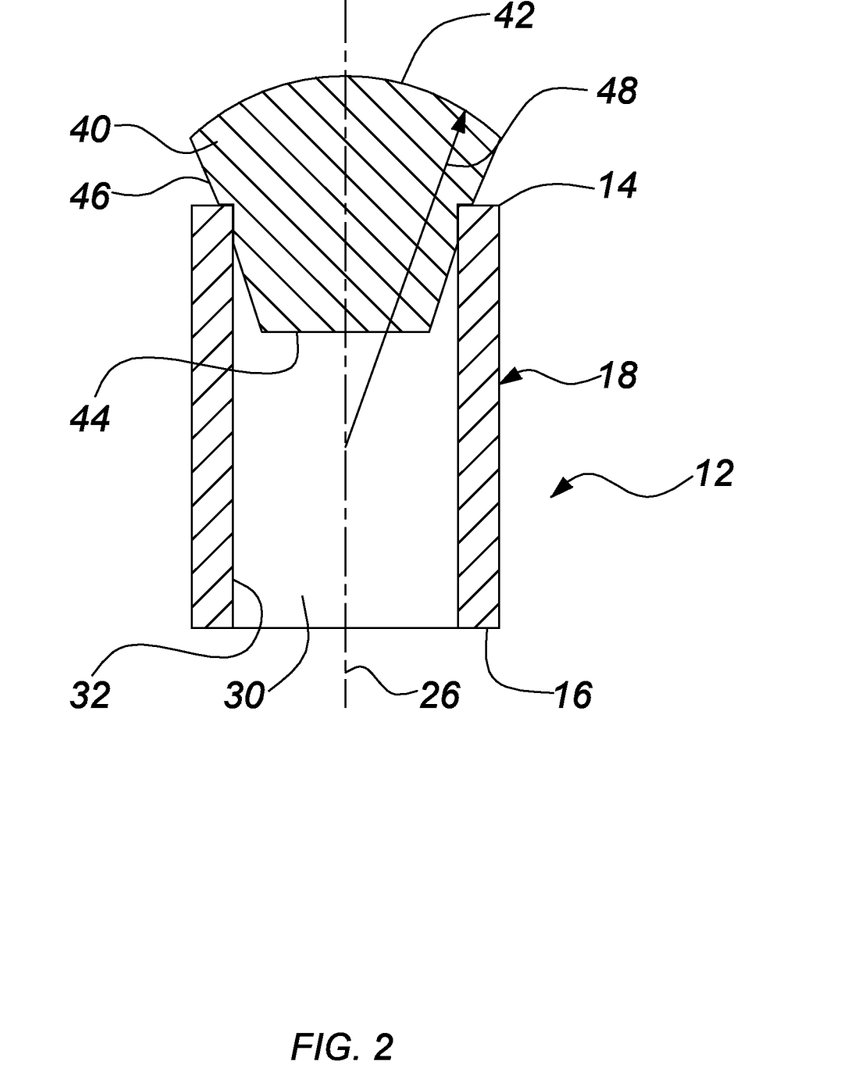
FIG. 2 is a cross sectional view of the apparatus of FIG. 2.
Figure 3:
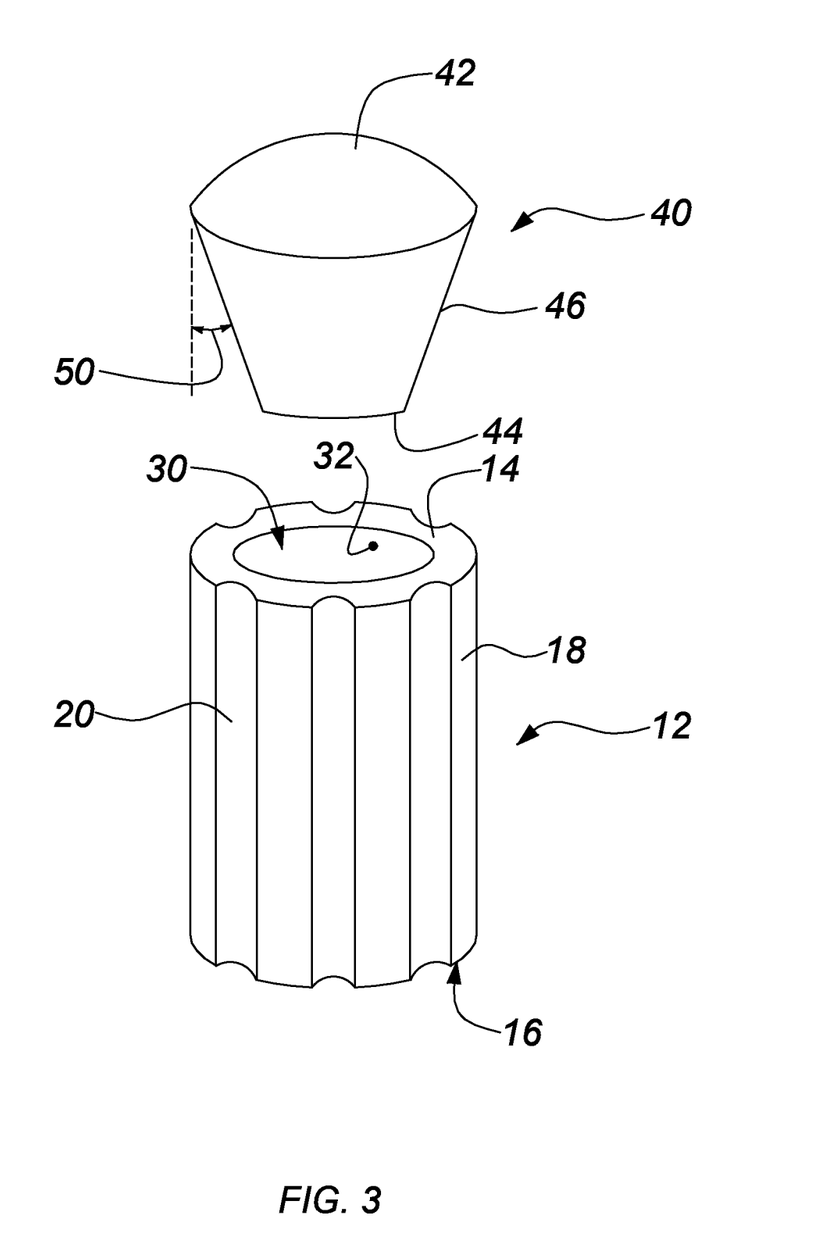
FIG. 3 is an exploded view of the apparatus of FIG. 2.

As illustrated in FIGS. 1 through 3, the handle body 12 comprises a cylindrical body extending between first and second ends, 14 and 16, respectively. The handle body 12 includes an outer surface 18 optionally having grooves 20 or other grip enhancing treatments thereon. The handle body 12 also include an inner surface 32 defining a bore 30 extending completely therethrough as illustrated in FIG. 2. As illustrated in FIG. 2, the handle body 12 may have a continuous profile extending along an axis 26 thereof so as to form a continuous unobstructed path through the bore 30 of the handle body for viewing therethrough by a user.

The image transfer body 40 comprises a plug adapted to be received within bore 30 of the handle body 12 in one of the first or second ends 14 or 16. The image transfer body extends between top and bottom surfaces, 42 and 44 respectively wherein the top surface 42 may be domed as illustrated. The image transfer body 40 includes an outer side surface 44 extending therearound between the first and second ends 14 and 16 which may optionally be tapered towards the bottom end 16 to aid in retention of the image transfer body within the bore 30 of the handle body 12. The top surface forms an image transfer surface adapted to transfer images to a nail as will be more fully described below and as illustrated in FIG. 2, may have a constant radius generally indicated at 48. The radius may be selected to provide a sufficient working surface to pick up the desired image when pressed thereupon while being small enough so as to not also pick up adjacent images. In practice it has been found that radii between 1 inch and 1.3 inches (25 and 33 mm) has been useful although it will be appreciated that other dimensions may also be useful depending upon the material selected for the image transfer body and the size of the images to be transferred. It will be appreciated other non-constant radius profiles may also be useful such as elliptical. It will also be appreciated that the profile to the top surface 52 may provide some magnification of the image when viewed through the apparatus 10 to assist in accurate image location. The image transfer body 40 is formed of a pliable transparent material so as to permit viewing therethrough. In particular, the image transparent body may be formed of a material selected from the group consisting of silicone, silicon rubber or the like such as Encapso® K distributed by Smooth On.

As set out above the sides of the image transfer body may be tapered to assist with retention of the image transfer body 40 within the bore 30 of the handle body 12. In particular the sides 46 may taper from a diameter larger than the bore 30 proximate to the top surface 42 to a diameter smaller than the bore 30 proximate to the bottom surface 44 and may be tapered along a taper angle indicated at 50 in FIG. 3. In practice it has been found that taper angles of up to 45 degrees have been useful although it will be appreciated that other angles may be useful as well. The bore 30 and the side wall 46 will be selected to have a cross-section corresponding to each other to ensure an secure fit therebetween. In particular as illustrated, bore 30 and side wall 46 may have a substantially circular cross section although it will be appreciated that other cross section shapes may be used, as well.

Figure 4:
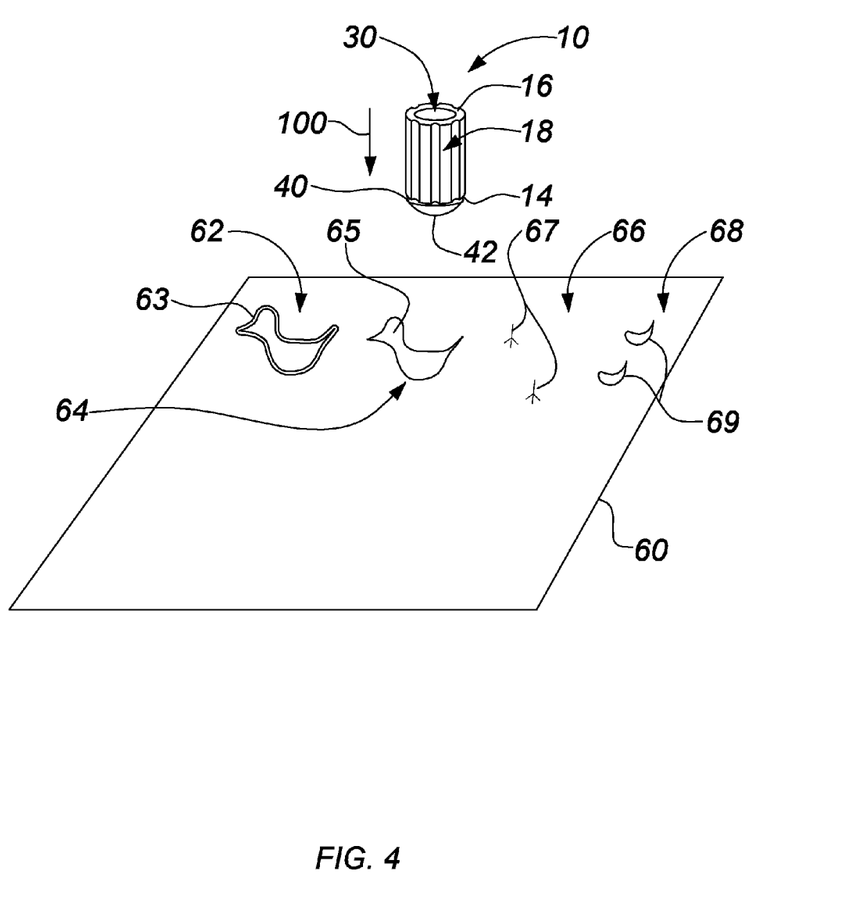
FIG. 4 is a perspective view of a process for forming a composite image using the apparatus of FIG. 1 and a plate for use with the apparatus of FIG. 2.

With reference to FIG. 4, a plate 60 may be utilized with the apparatus 10 for forming the composite image on the user's nail. The plate 60 includes a plurality of image locations 62, 64, 66 and 68 each having a depression, 63, 65, 67 and 69, respectively. Each of the image locations 62, 64, 66 and 68 corresponds to a different portion of the composite image which may have a different color of paint located within the depressions 63, 65, 67 and 69. In forming each image portion, paint may be located within the depressions 63, 65, 67 and 69 of the desired colors and the remainder scraped or otherwise removed leaving a portion of the image in that color within the depression. Thereafter, as illustrated in FIG. 4, the user may then utilized the apparatus to press the top or image transfer surface 42 onto each image to pick up the paint in each depression 63, 65, 67 and 69. It will be appreciated that permitting a user to view through the apparatus 10 including the image transfer body 40 permits accurate alignment of each image portion to ensure an accurate complete composite image. Furthermore as illustrated in FIG. 4, the image locations 62, 64, 66 and 68 may be aligned on the plate 60 so as to line up all the image locations 62, 64, 66 and 68 for that particular composite image. Furthermore, the image locations 62, 64, 66 and 68 may be arranged in order in which a user is to stamp or pick up the paint from that depression 63, 65, 67 and 69 is picked up by moving along that row. Although only a single image set it illustrated in FIG. 4, it will be appreciated that more than one image set may be contained upon a single plate. It will also be appreciated that although the composite image in FIG. 4 is formed of 4 parts, one at each image location, more or less than 4 may also be utilized.

Figure 5:
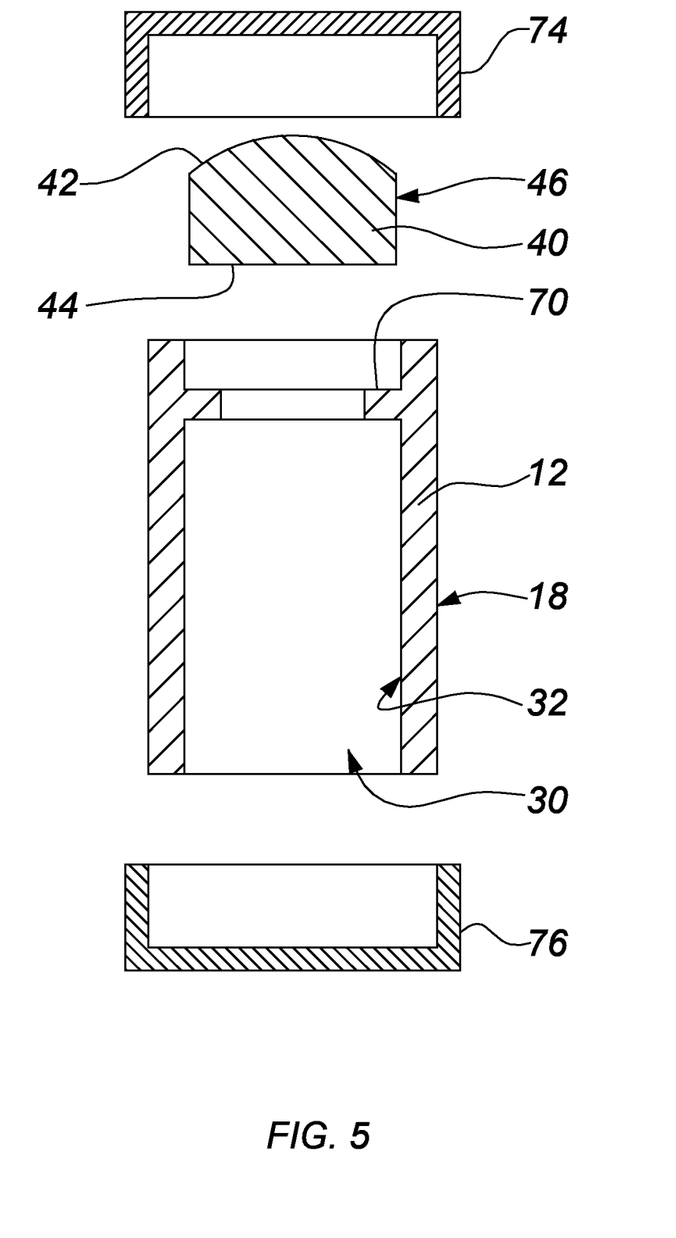
FIG. 5 is a cross sectional view of the apparatus for transferring images to the nail of a user according to a further embodiment of the present invention.
Figure 6:
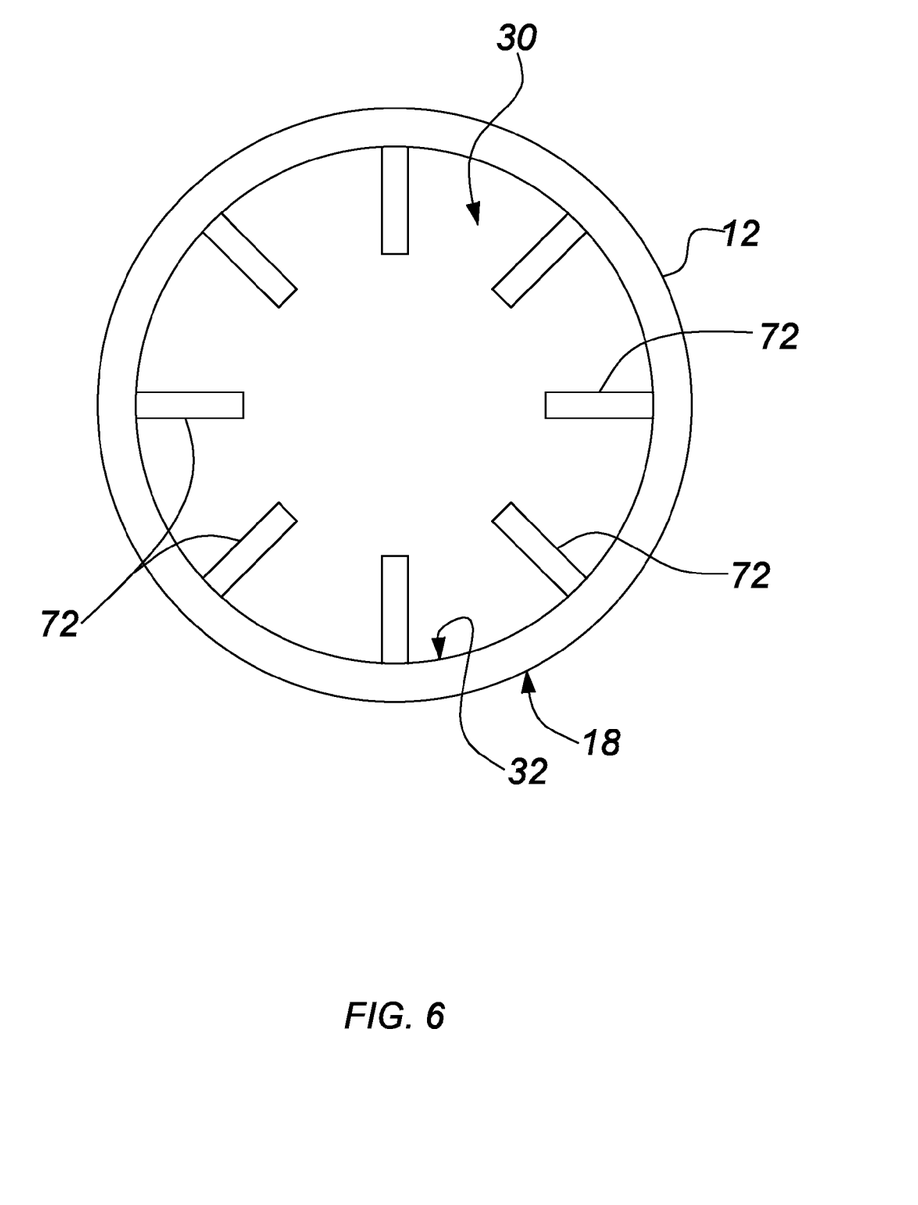
FIG. 6 is an end view of a handle for use in an apparatus for transferring images to the nail of a user according to a further embodiment of the present invention.

Turning now to FIG. 5, an optional embodiment is illustrated in which the handle body includes an annular wall 70 extending radially inwardly into the bore 30 thereof. The annular wall 70 is positioned to receive and support the image transfer body 40 at the desired location. As further illustrated in FIG. 5, the image transfer body may also optionally include a cylindrical side wall 46 to be fitted within the handle body 12. The wall 46 of the image transfer body 40 may be sized to be slightly larger than the bore 30 so as to provide a compression fit therein such as, by way of non-limiting example, up to ⅛ (3 mm) larger than the bore. The annular wall 70 may be continuous around the inside of the bore 30 or may optionally be segmented such as, by way of non-limiting example, being formed of radially spaced apart ribs 72 extending from the bore wall as illustrated in FIG. 6. As further illustrated in FIG. 5, the apparatus may also include first and second end caps, 74 and 76, respectively to enclose and contain the ends of the apparatus therein.

While specific embodiments of the invention have been described and illustrated, such embodiments should be considered illustrative of the invention only and not as limiting the invention as construed in accordance with the accompanying claims.

What is claimed is:

1. An apparatus for forming an image on the nail of a user comprising:
   a handle body extending between first and second ends and having an outer gripping surface and an inner surface defining a clear bore extending completely therethrough, said clear bore being unobstructed along the length of said handle body between permanently open first and second ends; and
   an image transfer body sized to be received within said permanently open first end of said bore of said handle body and being formed of a transparent non-permeable pliable material having an outer surface corresponding to said clear bore of said handle body and a top image transfer surface extending from said first end of said handle body, wherein said outer surface of said image transfer body is sized to be compressibly received within said first end of said bore, and wherein said first and second permanently open ends of said clear bore are defined by a free edge unconnected to external bodies.

2. The apparatus of claim 1 wherein said image transfer surface is substantially convex.

3. The apparatus of claim 2 wherein said image transfer surface has a substantially constant radius.

4. The apparatus of claim 1 wherein said outer surface of the image transfer body is tapered away from the image transfer surface to a narrower rear surface opposite said image transfer surface.

5. The apparatus of claim 4 wherein said outer surface of the image transfer body is frustoconical.

6. The apparatus of claim 4 wherein said outer surface of the image transfer body has a constant cross section therealong.

7. The apparatus of claim 1 wherein said image transfer body is formed of a material selected from the group consisting of clear silicon and rubber.

8. The apparatus of claim 1 wherein said handle body is substantially cylindrical.

9. The apparatus of claim 8 wherein said handle body may be formed of a tubular wall having a consistent cross section therealong.

10. The apparatus of claim 8 wherein said handle body includes an annular ledge extending substantially into said clear bore for supporting said image transfer body thereon.

11. The apparatus of claim 10 wherein said annular ledge is segmented around said clear bore.

12. A method of forming an image on a nail of a user comprising:

compressing a first end of an image transfer body formed of a transparent non-permeable pliable material;

locating said first end of said image transfer body within a clear bore extending completely through a handle body extending between permanently open first and second ends, said clear bore being unobstructed along the length of said handle body between permanently open first and second ends, so as to position a top image transfer surface of said image transfer body extending from said first end of said handle body, wherein said first and second permanently open ends of said clear bore are defined by a free edge unconnected to external bodies;

locating a portion of paint in a depression of a plate, pressing said image transfer surface on the image transfer body on the portion of paint to transfer the portion of paint to the image transfer surface and applying the image transfer surface to a nail of the user to transfer the paint to the nail.

13. The method of claim 12 further comprising repeating the steps of locating a portion of paint in a depression of a plate, pressing an image transfer surface on the image transfer body on the portion of paint to transfer the portion of paint to the image transfer surface a plurality of times.

14. A kit for forming an image on the nail of a user comprising the apparatus of claim 1 and a plate containing at least one image location having a depression adapted to contain a portion of paint to be transferred to a user's nail.

15. The kit of claim 14 wherein said plate includes a plurality of image locations each having a depression adapted to contain a portion of paint.

16. The kit of claim 15 wherein said plurality of image locations are divided into a plurality of image groups.

17. The kit of claim 16 wherein said plurality of image locations of each of said image groups forms a completed image when paint from each image location is overlaid on each other.

18. The kit of claim 16 wherein said image groups are aligned along a path across said plate.

\* \* \* \* \*